(12) United States Patent
Jewett

(10) Patent No.: US 6,831,467 B2
(45) Date of Patent: Dec. 14, 2004

(54) QSD RECOVERY OF SUPERPOSED TRANSIENT RESPONSES

(75) Inventor: Don Lee Jewett, Mill Valley, CA (US)

(73) Assignee: Abratech Corporation, Sausalito, CA (US)

(*) Notice: Subject to any disclaimer, the term of this patent is extended or adjusted under 35 U.S.C. 154(b) by 0 days.

(21) Appl. No.: 10/334,955

(22) Filed: Dec. 31, 2002

(65) Prior Publication Data

US 2003/0154057 A1 Aug. 14, 2003

Related U.S. Application Data

(63) Continuation-in-part of application No. 10/188,700, filed on Jul. 2, 2002.
(60) Provisional application No. 60/302,726, filed on Jul. 2, 2001.

(51) Int. Cl.[7] .............................. G01R 27/02; G06F 15/00
(52) U.S. Cl. ....................................... 324/605; 702/189
(58) Field of Search ................................ 324/605, 602, 324/600; 702/189, 127; 356/450, 451; 607/9, 14, 17, 19, 28, 32; 704/200, 258, 267; 708/100, 200, 400, 403, 405; 709/200, 201, 202

(56) References Cited

U.S. PATENT DOCUMENTS

| | | | |
|---|---|---|---|
| 5,546,956 A | 8/1996 | Thornton et al. | |
| 5,734,827 A | 3/1998 | Thornton | |
| 2001/0034493 A1 | 10/2001 | Stone | |
| 2001/0038277 A1 | 11/2001 | Stone et al. | |

*Primary Examiner*—Anjan Deb
*Assistant Examiner*—Hoai-An D. Nguyen
(74) *Attorney, Agent, or Firm*—Virginia H. Meyer, Esq.

(57) ABSTRACT

Apparatuses and methods for testing a system having a transient response that is longer than the intervals between stimulations, using a sequence of stimuli containing a small jitter. The timing sequence (called a q-sequence) is constrained by time-domain and frequency-domain rules. The system-response can be recovered from noise, despite response superposition, using deconvolution with a recovery sequence. The acronym QSD means "q-sequence deconvolution". The invention is especially applicable to signal processing of evoked-responses, including those used for disease screening.

23 Claims, 2 Drawing Sheets

QSD RECOVERY OF SUPERPOSED TRANSIENT RESPONSES

PRIORITY

This application claims priority from U.S. provisional application serial No. 60/302,726 filed Jul. 2, 2001 and U.S. application Ser. No. 10/188,700 filed Jul. 2, 2002, both of which are incorporated by reference herein. This application is a continuation-in-part of pending application Ser. No. 10/188,700.

GOVERNMENT RIGHTS

The invention was made with government support in the form of grants R43-NS26209, R44-DC00489, and R44-MH54922 awarded from the National Institutes of Health. The United States government has certain rights to the invention.

FIELD OF THE INVENTION

The present invention relates to signal processing apparatuses and methods. More particularly, the present invention relates to apparatuses and methods for recovering a transient waveform response from a signal comprised of an additive superposition of responses, such superposition occurring because the duration of a single transient response is longer than one or more of the intervals between the stimuli that cause the response.

BACKGROUND OF THE INVENTION

When a system is to be tested, it is common to control the input to the system and then observe the output of the system. In such a case, the input can be called a "stimulus", and the output called a "response". It is also common for a response to be sensed and transduced into an electrical signal that can be readily measured and/or converted into numbers (digitized) for subsequent analysis. It is also common for the stimulus timing to be controlled by a digitized number stream that is transduced or converted into a form appropriate to activate the system under test. It is also common to cyclically repeat the stimulus, either to average responses together, or to test whether the system-response is affected by the repetition-rate of the stimulation.

A problem arises when the test system-response is longer than the interval between stimuli. In such cases the measured electrical signal may be an algebraic summation of the individual responses, superposed in time. Such superposition may obscure features of the individual response that are of interest. Furthermore, if the superposition occurs when the pattern of stimulation is precisely periodic, i.e., when the interval from the start of a stimulus to the start of the next stimulus is always the same, then it is not mathematically possible to compute the individual response from the superposed signal. This is true because multiple solutions will be computed, with no possibility to determine which solution is correct, since the simultaneous equations that describe the waveform have more unknown variables than simultaneous equations.

As a result, it is necessary to test the system by a series of stimuli in which the SI (Stimulus Interval, start-to-start) in the series is not uniform, i.e., by a series of stimuli in which the stimulus repetition-rate "jitters".

One method for recovering the individual response from a superposed signal that uses a non-uniform stimulation sequence is called MLS (Maximum-Length Sequence). The MLS method is described in Thornton U.S. Pat. No. 5,546,956. An MLS is a pseudo-random sequence that has specific mathematical properties that permit easy calculation of a so-called "recovery function" that is cross-correlated to the superposed signal to recover the individual response.

To further discuss MLS and the invention, an SI-ratio is defined by: SI ratio=$(SI_{max}-SI_{min})/(SI_{min})$. The SI-ratio with MLS is always equal to, or greater than, unity. In some cases the MLS SI-ratio is more than 4. A major problem arises in the use of MLS if the system has responses that are affected by these SI differences Thus, MLS works if the system-response is SI-invariant, but fails if th system-response is SI-variant. Furthermore, it may not be possible to know if an error is present: if the tested system has a poor initial signal-to-noise ratio, then an SI-variant response may not be detected, yet can contribute to making the average of the response an inaccurate estimate of the system-response. Thus, there is a need for apparatuses and methods that can be used to estimate the individual system-response from an algebraic summation of superposed individual responses of a system under test, when such individual system response is SI-variant. The present invention fills this need.

Another problem arises if the system response is affected by the stimulus repetition-rate, i.e., is rate-variant. The invention uses a small SI-ratio. A small SI-ratio permits the apparatuses and methods of the invention to provide a point estimate of the system's response at a given repetition-rate to be obtained for comparison with the response at different repetition-rates. The invention can do this, even if the system is SI-variant, because the invention can use such a small variation in SI that the size of the waveform difference is made sufficiently small so as to be not significant to the user.

A specific application of the invention relates to analysis of sensory-evoked responses at repetition-rates that are above that of stimulus-fusion. Present methods do not permit accurate analysis because the evoked-responses are longer than the time between stimuli when the repetition-rate is high enough to cause perceptual fusion of the stimuli. Clearly, for this use, apparatuses and methods are needed that can accurately recover the evoked-response, for purposes of scientific investigation, clinical testing, or screening, including children and newborns. The present invention is generally applicable to so-called "Steady-State" responses that occur in several sensory-systems (Regan D, Human Brain Electrophysiology, (1989), Elsevier, N.Y., at pp. 34–42, 70–126, & 294–295), especially the auditory "40-Hz response" (Regan D, op. cit. at pp. 271–275).

SUMMARY OF THE INVENTION

The present invention provides apparatuses and methods for estimating the system-response WAVEFORM to each individual stimulus in a sequence of stimuli, from a system output composed of an algebraic summation of superposed individual responses of a system under test. The invention is especially useful when the individual system-response is SI-variant or mean-rate variant, or both. The invention teaches use of selected stimulation-sequences called q-sequences or quasi-q-sequences. Both q-sequences and quasi-q-sequences have a small variation in stimulus intervals, are pseudo-periodic, have a definitive time pattern, and conform to a rule-set with both time-domain and frequency-domain constraints. The frequency-domain constraints include the Fourier coefficient vector magnitude, referred to in the invention as "Q-magnitudes".

One of the time-domain constraints of q-sequences is a stimulus-interval ratio less than unity but greater than zero. One of the frequency-domain constraints of q-sequences is Q-magnitudes in the bandpass of interest of 0.5 or greater. One of the frequency-domain constraints of quasi-q-sequences is Q-magnitudes in the bandpass of interest less than 0.5 and greater than 0.01. Q-magnitudes can have values between zero and a number equal to the number of stimuli in the sequence.

The q-sequences and quasi-q-sequences are utilized for timing of stimuli in data-acquisition equipment that includes capabilities for stimulating the system under test, and for simultaneously recording the system output. The data-acquisition equipment can include additional components, such as: synchronizing means, averaging means, filtering means, amplifying means, data-rejection means, data-acquisition stopping means, simultaneous multiple q-sequence data-acquisition means, simultaneous multiple q-sequence data-acquisition means including at least one uniform stimulation-sequence means, Q-magnitude adjustment means, deconvolution set magnitude adjustment means, deconvolution set frequency adjustment means, data-analysis means, computational means, intermediate-data computational means, intermediate-data analysis means, display means, and outputting means.

The invention teaches data-analysis that utilizes deconvolution, which can be computed by any of a variety of methods. The use of deconvolution and q-sequences is indicated by the acronym for the methods of the invention: QSD (q-sequence deconvolution). The deconvolution is carried out on the recorded system output utilizing, in one form of the invention, a recovery sequence adapted from the reciprocal of the set of Q-magnitudes within the bandpass of interest combined with Q-magnitudes at the limit of the computer's floating point numbers in bandreject regions. In one form of the invention, the frequency-domain components making up the recovery sequence can be selected, modified, or adjusted to improve recovery of the system-response.

If averaging is included in the data analysis, the deconvolution can occur before or after averaging. The data-analysis equipment can include additional components, such as: synchronizing means, alignment means, input means, averaging means, filtering means, amplifying means, noise-estimation means, data-rejection means, sweep-rejection means, simultaneous multiple stimulation-sequence data-analysis means, simultaneous multiple stimulation-sequence data-analysis means including at least one uniform stimulation-sequence means, decimation by frequency means, decimation by time means, Q-magnitude adjustment means, deconvolution-set magnitude-adjustment means, deconvolution-set frequency-adjustment means, computational means, intermediate-data computational means, intermediate-data analysis means, waveform-analysis means for analyzing said estimated system-response waveform, display means, outputting means, deconvolution by time-domain convolution of the system output by a convolution recovery sequence means, deconvolution by time-domain cross-correlation of the system output by a cross-correlation recovery-sequence means, deconvolution by division in the frequency-domain of the system output by a deconvolution set of Fourier coefficients means, deconvolution by multiplication of said system output by an inversion of a circulant matrix derived from a convolution recovery sequence means, filtering in the time-domain means, filtering in the frequency-domain means, deconvolution of single sweeps, deconvolution of combinations of one or more single sweeps, deconvolution of subaverages, deconvolution of system output without use of alignment-signal means.

The data-acquisition and the data-analysis of the present invention can be practiced using a digital computer as a component of the invention. Other equipment variations are possible. For example, the stimuli can be timed and shaped from some device such as a compact-disk player, a digital-video-disk player, an MP3 player, a video-tape player, an audio-tape player, a digital-memory player, or the like, each containing a previously-recorded storage medium or the like. Stimuli could also be delivered from a remote location using various communication means, such as cable transmission means, or radio frequency means, or satellite means.

For some practical applications, it may be desirable to separate the invention's functions either physically or functionally. For example, the data-acquisition functions could be performed in one set of equipment, on-line, and then the data-analysis performed in other equipment, off-line. In this case the data-analysis equipment could be separated from the data-acquisition equipment by many miles, and even by time. There might be internet or stored-media communication between two such separated sets of equipment.

The invention has important applications to sensory evoked-responses at stimulus repetition-rates higher than perceived stimulus fusion because some evoked-response waveforms superpose at these repetition-rates. One such waveform is shown in FIG. 2, which is discussed in Example One found at the end of the Description section of this specification. Sensory evoked-responses have wide utility for clinical testing and disease screening, including testing newborns.

The estimated system-response waveform produced by the invention may not be the ultimate goal of the user. In such a case there may be additional processing of the information in the waveform. For example, if the invention is used in screening tests, an automatic evaluation of the estimated system-response waveform may yield a "pass/no-pass" output only.

While the disclosed invention must be used to obtain an accurate estimate of the system-response waveform when testing a system in which the individual system-response is SI-variant and/or mean-rate variant, the invention is not limited to such systems. The invention's waveform-estimate recovery method is fully applicable to systems in which the system-response waveform is SI-invariant and/or mean-rate invariant. For example, the present invention can be used in most applications where MLS is utilized to recover the system-response waveform since the successful use of MLS for system-response recovery implies that the response is SI-invariant and mean-rate invariant.

BRIEF DESCRIPTION OF THE DRAWINGS

FIG. 2, column B shows individual responses deconvolved from the data of column A.

DESCRIPTION OF THE INVENTION

Figure 1:
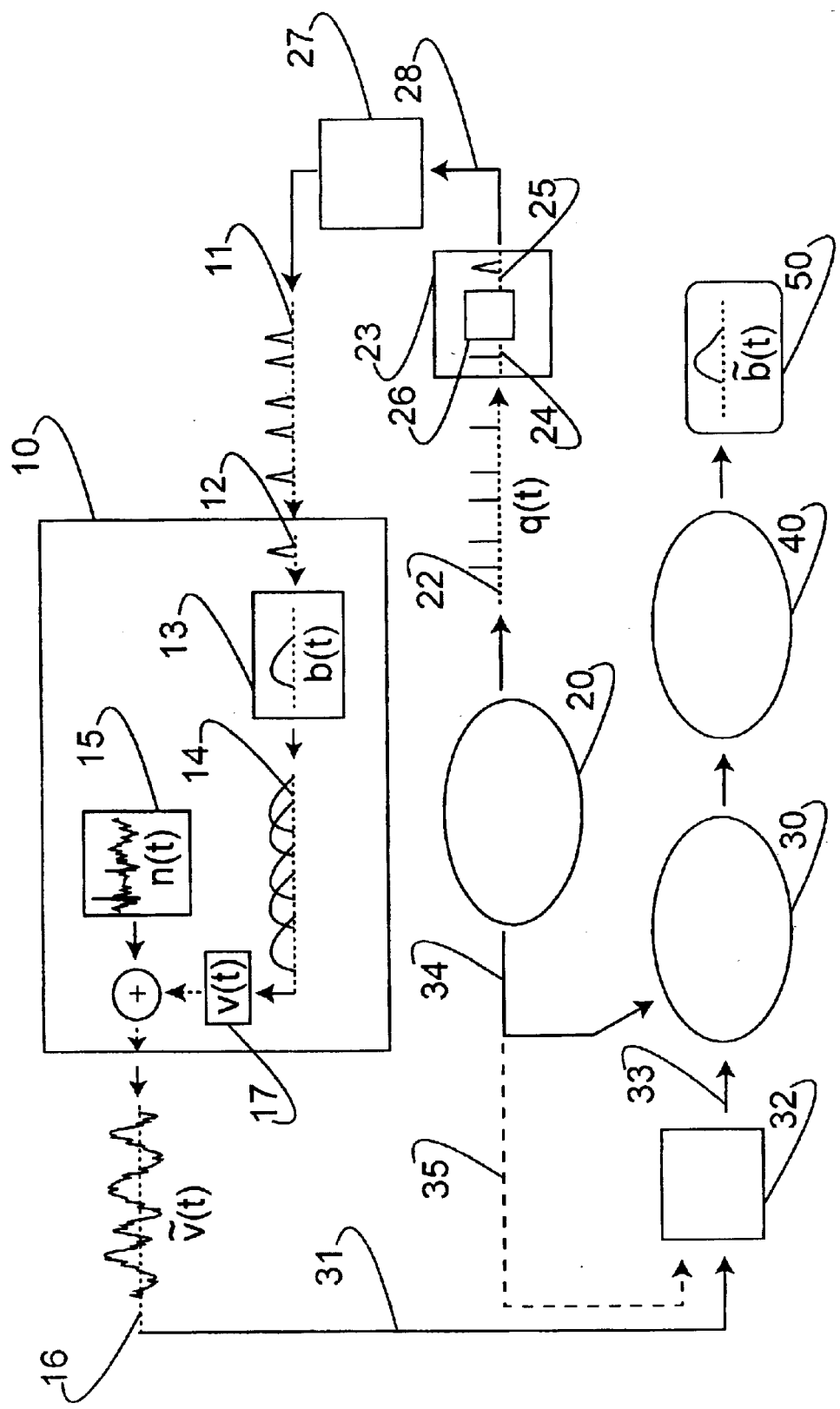
FIG. 1 is a block diagram showing the invention used to test a responding system.

The present invention is apparatuses and methods for estimating a transient system-response waveform that is longer than the intervals between stimulations, the estimate being based on the superposed responses.

As those skilled in the art will realize, the invention is most accurately described by the equations included later in the Description section. However, as an aid to visualization, the invention is first described as it is diagramed in FIG. 1. When system 10 is stimulated, or "activated", by a single transient input called a "stimulus" 12, the transient result is called "response", shown in box 13. If the duration of response in box 13 is longer than the time between stimulations in stimulus sequence 11, then the individual response-waveforms from box 13 can overlap. Since superposition of overlapped way forms (v(t) in box 17) comprises algebraic summation at individual time-points during the superposition, response-waveform in box 13 may be obscured, or obliterated, in system output 16, even if the noise shown in box 15 is small or non-existent.

In engineering, a "black-box approach" involves study of the "transfer function" relating output to input as might be applied to box 13. As will become apparent to someone skilled in such engineering art, the invention is not affected by, or related to, possible non-linearities in box 13, or other aspects of the transfer function of box 13. If the timing pattern of timing sequence 22 carries through to system output 16 due to superposition, then deconvolution can be used to estimate the response in box 13 even though the response in box 13 is a non-linear function of single stimulus 12, and even if the response in box 13 is a non-linear function of the mean time-interval in timing sequence 22.

Sequence-control means 20 produces the timing pattern of timing sequence 22 that in one embodiment is timing from a digital computer binary output that activates stimulus sequence creation means 23, which includes stimulus shaping means 26. Stimulus shaping means 26 takes as an input single-stimulus timing signal 24 and creates shaped single-stimulus 25 that is outputted by stimulus sequence creation means 23. Stimulus sequence creation means 23 energizes stimulus generating means 27 via shaped-stimulus communicating means 28. Stimulus generating means 27 can include energy transduction, if necessary. By the means described, sequence-control means 20 controls the timing of the stimuli in stimulus sequence 11. Stimulus sequence 11 stimulates system 10.

Within system 10, single stimulus 12 causes single system-response waveform shown in box 13. When the SI (Stimulus Interval start-to-start) in stimulus sequence 11 is shorter than the duration of the system-response waveform shown in box 13, then superposition of response waveforms (v(t) in box 17) can occur in system output 16 together with additive noise shown in box 15. System output 16 is collected and transported by system output communicating means 31 to analog-to-digital converter means 32, whose output 33 is data that is received and stored in data-acquisition means 30. Aligning signal 34 or 35 is acquired by data-acquisition means 30 simultaneously with system output 16. Aligning signal 34 or aligning signal 35 can be one of the following: a signal time-correlated to timing-sequence 22, timing sequence 22, or stimulus sequence 11.

Data-acquisition means 30 transfers the system output data and the aligning signal to data-analysis means 40. Data-analysis means 40 performs a variety of mathematical computations on the data and aligning signal, transmitting to display means 50 an estimation of system-response waveform shown in box 13 of system 10 to single transient stimulus 12.

Aligning signal 34 or aligning signal 35 is used to correlate system output 16 with timing sequence 22. In one embodiment, either aligning signal consists of a unique pattern from which the start of the timing pattern of timing sequence 22 can be aligned relative to system output 16. Such alignment is necessary since in a cyclic repetition of timing sequence 22, the Q-magnitudes are the same no matter what the starting point of the sequence, but the phase relationships differ with every starting point. The recovery functions utilize both Q-magnitudes and phase relationships to recover estimated waveform $\hat{b}(t)$. Thus, the starting point is necessary for recovery of estimated waveform $\hat{b}(t)$, and the starting point can be determined from aligning signal 34 or aligning signal 35.

In another embodiment, aligning signal 34 or 35 can consist of the timing pattern of timing sequence 22 or stimulus sequence 11. In either case the starting point can be ascertained for data analysis means 40 by cross-correlating a template of recorded aligning signal 34 or 35 with that acquired in data-acquisition means 30. The maximum cross-correlation will provide the alignment.

In another embodiment, aligning signal 34 or 35 is not used. Data analysis means 40 repeatedly calculates estimated waveform $\hat{b}(t)$ at different phase relationships between the acquired system output 16 and timing sequence 22. The calculation yielding the best waveform based upon previously-established user criteria is taken as estimated waveform $\hat{b}(t)$.

In one embodiment, in which the digital-to-analog rate of sequence-control means 20 does not equal the rate of analog-to-digital means 32, alignment signal 34 or 35 provides a means to ensure alignment of the timing pattern of timing sequence 22 with A-D output 33 in data-acquisition means 30 or data-analysis means 40. In either data-acquisition means 30 or data-analysis means 40 the simultaneously-recorded alignment signal is used to determine the repeated starting of timing sequence 22. Times will occur when there are too many time-points or too few time-points in D-A output 33 because of the different rates. When this occurs either data-acquisition means 30 or data-analysis means 40 can add an interpolated data-point if there are too few points, or drop a data-point if there are too many With modern digital equipment, the rates are sufficiently high that the error introduced is not significant.

In one embodiment of the invention, sequence-control means 20, stimulus sequence creation means 23, stimulus shaping means 26, stimulus generating means 27, data-acquisition means 30, analog-to-digital converter means 32, data-analysis means 40, and display means 50 can each be in a physically-separate unit. In other embodiments these means can be in any combination or permutation of physically-separate or physically-combined units. For example, in one embodiment stimulus sequence creation means 23, stimulus shaping means 26, and stimulus generating means 27 may be in one physically-combined unit that might be called a "stimulator". Such a stimulator might produce a finite-duration vibratory output for each single-stimulus timing signal 24. Another stimulator might produce a finite-duration photic stimulation for each single-stimulus timing signal 24. Yet another stimulator might produce a shaped tonal stimulus for each single-stimulus timing signal 24. In another embodiment, sequence-control means 20 and stimulus sequence creation means 23 are combined in a single physical unit, such as a compact-disc player, digital-video-disk player, MP3 player, video-tape player, audio-tape player, radio receiver, video receiver, and the like. In such an embodiment, the timing pattern of timing sequence 22 and the shape of single transient stimulus 12 have already been combined and stored so that the timing of stimulation-sequence 11 and the shape of each stimulus is transmitted by shaped-stimulus communicating means 28 that controls stimulus generating means 27. In such an embodiment, stimulus generating means 27 is an energy transducer, such as an amplifier.

In any embodiment, stimulus sequence creation means 23 and stimulus generating means 27 can each include additional components, such as: amplifying means, filtering means, communication means, transduction means, energy-conversion means. In any embodiment, system output communicating means 31 can include additional components, such as amplifying means, filtering means, signal transduction means, and energy-conversion means.

In one embodiment, sequence-control means 20 and data-acquisition means 30 are combined in a single unit, which could be a digital computer. In another embodiment, data-acquisition means 30 and data-analysis means 40 are combined in a single unit, which could be a digital computer. In yet another embodiment, sequence-control means 20, data-acquisition means 30, and data-analysis means 40 are combined in a single unit, which could be a digital computer. In one embodiment, when equipment is separated, data-analysis means 40 might be a general-purpose computer with associated software, with such computer having inputing means including but not limited to internet connections, ethernet connections, local-area network connections, telephone connections, wireless communications, or storage-media access.

In one embodiment, analog-to-digital converter means 32 is time-synchronized with the timing of timing sequence 22, such that data-acquisition means 30 can convey to data-analysis means 40 the precise timing of each spike in timing sequence 22 together with the corresponding precise synchronized output of the analog-to-digital converter means 32. Where stimulus sequence creation means 23 contains a digital-to-analog converter, such a converter can be operated at the same frequency as the analog-to-digital converter means 32, but this is not a requirement of the invention. For example, analog-to-digital converter means 32 and stimulus sequence creation means 23 may operate at different cyclic rates. In such an embodiment, alignment signal 34 or alignment signal 35 can be used for time-synchronization between system-response output 16 and timing sequence 22. In another embodiment, there is no aligning signal from sequence-control means 20 and data-analysis means 40 does additional computations to determine estimated waveform $\tilde{b}(t)$.

In one form of the invention, both analog-to-digital converter means 32 and sequence-control means 20 operate continuously with a 100% duty cycle. In another form of the invention, only analog-to-digital means 32 operates continuously with a 100% duty cycle.

In order to describe the computations involved in this process, mathematical terminology is used. The terminology is listed and defined in the Table, below. The following description assumes that time, t, is discretized by cyclic analog-to-digital conversion. See FIG. 1 to note the following equivalences. The stimulus timing pattern of timing sequence 22 is q(t). System 10 single system-response waveform shown in box 13 is b(t). Superposition of b(t) is v(t) in box 17. Noise in box 15 is n(t). The combination of v(t) and n(t) is $\tilde{v}(t)$, which is system output 16 in analog form and is output 33 of analog-to-digital converter 32 in digital form. Estimation of b(t) by data-analysis means 40 is $\tilde{b}(t)$ displayed in display means 50.

For the purposes of this invention, the following definitions pertain. A "stimulus interval" (SI) is the time from the start of one stimulus to the start of the next stimulus. Such timing is determined by the time intervals between successive binary 1's in the stimulation-sequence q(t). "Pseudo-periodic sequence" is defined as being a sequence of stimuli in which the SIs are not uniform, and where the SI-ratio is between 0 and 1. The "SI-ratio" is quantified by the definition: SI ratio=$(SI_{max}-SI_{min})/(SI_{min})$. When the SI-ratio=0, the SIs are uniform. An SI-ratio equal to 1 is the ratio that distinguishes for the purposes of this invention pseudo-periodic sequences from pseudo-random sequences. When there is a uniform sequence in which a single stimulus is removed, then the SI-ratio=1. This is equivalent to one stimulus having been "jittered" over to the next stimulus in the uniform sequence, which is the maximum jitter possible in such a sequence. For the purposes of this invention, a stimulus sequence that has an SI-ratio greater than 1 is not pseudo-periodic.

One goal when using the invention is to make the SI-ratio as small as possible, consistent with factors such as the system noise, and the degree that the system-response waveform is SI-variant. With an SI-variant system-response, the error can be reduced by reducing the jitter, i.e., by reducing the SI-ratio. The size of SI-ratio that is required is dependent upon the amount that the system-response waveform changes with SI. A small change in system-response waveform with a large change in SI means that a large SI-ratio can be used, whereas a large change in system-response waveform means that a small SI-ratio is needed. The goal is to use an SI-ratio in which the amount of change in SI causes a change in system-response waveform that is insignificant as judged by the user. The reason that the user cannot just always use a small SI-ratio is that the smaller the SI-ratio, the longer the sequence-length needed to find adequate Q-magnitudes in the bandpass, which in turn lengthens the data-run. The invention described herein has been successfully used on an SI-variant system when the SI-ratio was less than 0.25, as shown in the Example One.

A q-sequence with an SI-ratio in the range of 0.7 to 1 has a large amount of jitter and is undesirable for some applications. A q-sequence with an SI-ratio in the range of 0.5 to 0.7 is acceptable for some applications, but not for others. A q-sequence with an SI-ratio in the range of 0.3 to 0.5 is often good, and a q-sequence with an SI-ratio in the range of 0.15 to 0.3 is often excellent.

The superposed v(t) is equivalent to b(t) convolved with q(t) (Eq. 1).

$$v(t)=b(t) \copyright q(t) \tag{1}$$

where ©=special-case convolution (i.e., convolution in which q(t) is limited to binary 1's and 0's).

Because of the inevitable presence of noise, Eq. 1 must be modified to include noise, as shown in Eq. 2.

$$\tilde{v}(t)=[b(t) \copyright q(t)]+n(t) \tag{2}$$

The stimulation-sequence, q(t), is called a "q-sequence". A q-sequence is pseudo-periodic, meaning that the SI are not uniform, but are "jittered" by small amounts. The means of creating q-sequences are given below. The process of deriving from $\tilde{v}(t)$, an estimate [$\tilde{b}(t)$] of the original waveform [b(t)], using q-sequences, is called "QSD" (q-sequence deconvolution). Deconvolution can be accomplished numerically in a variety of ways, some of which are described later.

It will now be shown how to design q-sequences that are useful in QSD. As is known to those skilled in the art, in transferring Eq. 2 to the frequency-domain, the convolution becomes a multiplication, as shown in Eq. 3.

$$\tilde{V}(f)=[B(f) \cdot Q(f)]+N(f) \tag{3}$$

To deconvolve in the frequency-domain, Eq. 3 is divided by Q(f) (Eq. 4).

$$\frac{\tilde{V}(f)}{Q_d(f)} = \frac{B(f) \cdot Q_c(f)}{Q_d(f)} + \frac{N(f)}{Q_d(f)} \qquad (4)$$

In Eq. 4 the subscripts c and d stand for convolution and deconvolution, respectively. Both $Q_c(f)$ and $Q_d(f)$ are specified because the processes by which they are manipulated and used are different, and in QSD they are sometimes not equal. The convolution set $\{Q_c(f)\}$ is a property of the stimulation-sequence and can only be altered by changing the stimulation-sequence. On the other hand, the deconvolution set $\{Q_d(f)\}$ consists of numbers utilized in the waveform recovery. That is, $\{Q_d(f)\}$ are utilized to compute r(t), as described later. If subscripts are not shown, then $Q_c(f) = Q_d(f)$.

Each Q(f) is a complex number. For computational purposes the complex number is always used in QSD. A complex number can be represented in rectilinear coordinates with real and imaginary axes, or in polar coordinates by a vector having a magnitude and an associated angle. In some aspects of QSD the importance of a Q(f) is in relation to the vector magnitude, which we will call a "Q-magnitude", and represent as $|Q(f)|$.

Note that in Eq. 4, B(f) is multiplied by $Q_c(f)$, whereas N(f) is not. Thus, $|Q_c(f)|$ can alter the SNR(f) (Signal-to-Noise Ratio at a given frequency), whereas $|Q_d(f)|$ cannot because in Eq. 4 $|Q_d(f)|$ is in the denominator of both the signal and the noise.

Eq. 5 shows the factors that contribute to SNR(f).

$$SNR(f) = \frac{[|B(f)| \cdot |Q_c(f)|]/|Q_d(f)|}{|N(f)|/|Q_d(f)|} \qquad (5)$$

$$= \frac{|B(f)| \cdot |Q_c(f)|}{|N(f)|} \qquad (5A)$$

$$= \frac{|B(f)|}{|N(f)|/|Q_c(f)|} \qquad (5B)$$

Note that $|Q_d(f)|$ is not on the right-hand side of Eqs. 5A and 5B, showing that it does not affect SNR(f). However, adjustments to the set $\{Q_d(f)\}$ do affect the overall detection of the time-domain signal, as will be explained later.

From Eq. 5 it is clear that if $|Q_c(f)|$ is less than unity, it will reduce the SNR(f). The reduction can either be seen as having decreased the signal (because the product $|B(f)| \cdot |Q_c(f)|$ is lessened—Eq. 5A) or increased the noise (because the quotient $|N(f)|/|Q_c(f)|$ is greater—Eq. 5B). Whereas if $|Q_c(f)|$ is greater than unity, it will increase the SNR(f). In general, it is desirable for the SNR to be as large as possible, so it is desirable for a stimulation-sequence to have large values of $|Q_c(f)|$. If a stimulation-sequence has a very small $|Q_c(f)|$ at some frequency, it is possible that the increase in noise at that frequency following deconvolution with a small $|Q_d(f)|$ at that frequency might obscure the signal after the frequency-domain data is transformed into the time-domain.

The magnitudes of $|Q_c(f)|$ are found by computing a simplified Fourier transform of the binary stimulation-sequence q(t) (Eq. 6).

$$|Q_c(f)| = \sqrt{\left[\sum_{s=0}^{\#s-1} \cos(g_f \omega_s)\right]^2 + \left[\sum_{s=0}^{\#s-1} \sin(g_f \omega_s)\right]^2} \qquad (6)$$

where:

$|Q_c(f)|$ is the Fourier coefficient vector magnitude for a specific frequency (f), and is the vector sum of the real and imaginary Fourier components.

$g_f$ is derived by dividing f by the primary frequency, where the primary frequency is the inverse of the sequence-length. $g_f$ is usually an integer, but in some embodiments need not be.

s is the total number of stimuli in the sequence-length.

s is the sequential numbering of the stimuli in the sequence-length.

$\omega_s$ is the timing of the s-th stimulus in the stimulation-sequence, taken as a fraction of the sequence-length, expressed as an angle.

Note that there are no magnitude-multiplier functions in Eq. 6, as there are in a full Fourier-coefficient computation, because of the special-case of the binary stimulation-sequence wherein the magnitude of each bin indicating a stimulation time is unity and the rest of the bins are zero. Note further that the Fourier 1/N factor is not in this equation. This factor is part of the inverse function of QSD so that the critical value of $|Q(f)|$ is unity when evaluating stimulation-sequences using Eq. 6.

It will be evident to one skilled in the art that the maximum Q-magnitude that can be obtained from Eq. 6 is equal to the number of stimuli in the stimulation-sequence for which the Q-magnitudes are being computed. It will also be evident that the minimum Q-magnitude is zero, this value being obtainable only if the stimulation-sequence has no jitter.

To apply QSD the stimulation-sequence (q(t)) should be selected. The selection of a stimulation-sequence is based on several factors that can be chosen by the user, for example:

1. The desired mean SI.
2. The range of permitted jitter.
3. The SL (Sequence Length). The duration of the SL must be longer than the duration of the response. The SL also determines the period of $g_1$ (Eq. 6) and affects the length of a data-acquisition run (which is either the SL or the SL times the number of sweeps averaged). A judicious choice of SL length also can act to cancel 60 Hz and 120 Hz interference where the SL is an odd multiple of ½ the period of 120 Hz and the number of sweeps averaged is always a multiple of 4.
4. The bandpass of interest in which the Q-values should be near, or above, unity.
5. The rate of digitizing of analog signals. Too low a rate may make finding q-sequences difficult or impossible for reasons described in the next paragraph.

The Q-magnitudes ($|Q_c(f)|$) are altered by varying the stimulation points on SL within the constraints created by the user's choice of factors. The A-D rate determines the smallest change in time that can occur when one of the SIs is changed. With a low A-D rate the smallest change possible can be larger than the maximum SI permitted by the user's choice of SI-ratio. In such a case the SI cannot be varied finely enough to obtain adequate Q-magnitudes. As an example, in the recordings shown in Example One, if the A-D rate were at 300 Hz, which is the minimum sampling rate for the 30–150 Hz bandpass, the A-D period would be 3.3 ms. This A-D rate would not permit a stimulation-sequence having a jitter maximum of ±12% at a mean SI of 24 ms, because the maximum jitter permitted by the limit is 2.9 ms, yet the minimum jitter possible from the A-D rate is 3.3 ms. Whether an A-D rate is sufficiently fast is determined during the selection of the stimulation-sequence as described in the next paragraph.

The factors listed above included a bandpass of interest. For use in the present invention, the bandpass of interest is defined as the bandpass needed to display or use the estimated response waveform $\hat{b}(t)$. The reason that a bandpass of interest is needed in the user's constraints is that it may not be possible to obtain an adequate estimated response waveform $\hat{b}(t)$ without such a bandpass, as will now be explained. With small SI-ratio, it is common for some of the Q-magnitudes out of the entire set of Fourier frequencies to be significantly less than unity, where the significance relates to how much the Q-magnitude increases the noise at that frequency. These Q-magnitudes can be called "poor". If the entire set is used in the deconvolution, the result will be unsatisfactory because the time-domain waveform will contain components with increased noise from the frequencies with poor Q-magnitudes. If the frequencies with poor Q-magnitudes are outside the bandpass of interest they can be filtered without affecting the waveform of interest while the signal can be recovered accurately if $|Q_d(f)|=|Q_c(f)|$ within the bandpass. However, if the poor Q-magnitudes occur in frequencies within the bandpass of interest, the only choices are either to recover the waveform with a poor SNR(f), or to adjust the $Q_d(f)$, which will distort the signal portion of the time-domain waveform. It is better to find another stimulation-sequence that has "good" Q-magnitudes in the bandpass. Variation in Q-magnitudes at specific frequencies by changing the position of stimuli in a stimulation-sequence is possible because of Parceval's theorem, which has the consequence that two q(t) of the same length and containing the same number of stimuli will have the same integrated Q-power in the frequency-domain. Thus, keeping the length and number of stimuli the same, when the SIs within these constraints are varied, the Q-magnitudes can vary. It is a teaching and an aspect of the invention to select the stimulation-sequence to keep "poor" Q-magnitudes outside the bandpass, while permitting accurate waveform recovery within the bandpass.

For a given stimulation-sequence, the set $\{|Q_c(f)|\}$ within the bandpass of interest is readily calculated from Eq. 6. An iterative search can be used to find a workable stimulation-sequence based upon evaluating the Q-magnitudes of the $\{|Q_c(f)|\}$ set relative to a cost function in a computerized stimulation-sequence selection. It should be noted that a user may inadvertently choose constraints that are mutually incompatible. (One example was given above with regard to maximum jitter and A-D rate.) The user may then be unable to find a useful q-sequence. The user must then modify or revise the constraints and search again.

Since the search for the stimulation-sequence is a multiple-variable constrained optimization, there are a variety of computational methods known to those with knowledge of the art that can be applied. The specific optimization technique used is not critical. Suitable techniques include: simulated annealing (Press et al., *Numerical Recipes in C, The Art of Scientific Computing*, 2nd Ed., (1992) Cambridge Univ. Press, Cambridge, at Chap. 10.9; also available for the Matlab computer program at http://www.mathworks.com/, accessed on Jun. 24, 2002); Tabu (Glover, F., *ORSA Journal on Computing*, Summer 1989, vol. 1, (No. 3), at pp. 190–206); genetic algorithms; and global optimization techniques resistant to local minima. Essentially, the optimization technique repeatedly generates stimulus sequences and selects those that minimize some "cost function" within the prescribed constraints (the constraints including, but not limited to: number of stimuli, mean SI, maximum SI-ratio, sequence length, and sampling rate). For example, the cost function might minimize the number of Q-magnitudes that are below unity within a desired bandpass. For another example, the cost function might require all Q-magnitudes in the bandpass of interest to be greater than unity. A description of the use of simulated annealing to find a q-sequence is given in Example One.

The q-sequence search can include other constraints on q(t) that are desired by the user, including, but not limited to, presence or absence of a specific stimulus pattern, interposed correlated or uncorrelated stimuli, asymmetrical limits of jitter relative to the mean, pauses, harmonic SIs, minimum or maximum Q-magnitude differences, and/or a sequence length that cancels AC interference.

If the q-sequence is not selected by evaluating the effects of the sequence pattern on $|Q_c(f)|$, as might occur by randomly generating the sequence, then the sequence can have one or more $|Q_c(f)|$ that are significantly less than unity in the bandpass of interest. The consequence of a $|Q_c(f)|$ significantly less than unity is that if $|Q_d(f)|$ at that frequency is made equal to $|Q_c(f)|$ so that the response can be accurately recovered, then the noise at that frequency will be made larger, as is shown by $|Q_d(f)|$ being in the denominator of the fraction $|N(f)|/|Q_d(f)|$ in Eq. 4. Clearly, noise is "significant" in the frequency-domain if it dominates the signal when transformed into the time-domain. This phenomenon may occur in methods that utilize random sequences.

In contrast to random and pseudo-random sequences, q-sequences are pseudo-periodic, which implies that the q-sequence approximates to periodicity, not to randomness. Also, q-sequences are not "true random" sequences, where "true random sequences" have been defined as being "substantially devoid of a definitive pattern or relationship with time" by inventors Stone, Robert T., et al., in printed U.S. patent application publication number 20010036277. In contrast, a q-sequence contains a definitive time pattern, where the term "definitive time pattern" is defined for this invention as being a pattern that conforms to a rule set containing both time-domain and frequency-domain rules.

The need for the q-sequence to have a definitive time pattern can be readily shown. If the SIs of a q-sequence that meets given user constraints are re-ordered (i.e., the same SIs are re-arranged into a different time pattern), the Q-magnitudes are likely to be different and unsatisfactory That is, for a given set of SIs, only some orderings of those SIs will have satisfactory Q-magnitudes in a given bandpass. This fact can be understood by realizing that the Q-magnitudes are the magnitudes of the harmonics of the base frequency of the q-sequence. The base frequency is determined by the length of the sequence. The harmonics are multiples of the base frequency, and are given by the values of $g_f$ in Eq. 6. Successful use of this invention requires that the harmonic frequencies of interest in the bandpass are accentuated by the stimulation-sequence. This accentuation is measured by the Q-magnitudes, which are preferably greater than, or near, unity in the bandpass. The ordering of SIs affects the harmonic frequencies, and hence affects the Q-magnitudes. So, not only does the size of the individual SI matter as to whether a given sequence meets the requirements of the user, but also the order. Clearly, such requirements are not met by a set of random SIs. In contrast, the requirements are met only by a definitive time-pattern, that time-pattern being determined by the criteria used in the stimulation-sequence selection. As indicated above, the time-pattern of a q-sequence is defined by a rule set that contains both time-domain and frequency-domain constraints. The time-domain constraints relate to the mean SI and to the permitted SI-ratio, among others. The frequency-domain constraints relate to the Q-magnitudes. The q-sequence rule set requires that the Q-magnitudes in the frequency-domain be 0.5 or greater in the bandpass of interest. While there is no known analytic method to go from a frequency-domain Q-magnitude rule set to a time-domain q-sequence, this problem is readily solved by one skilled in the art, by repeated generation and testing of q-sequences in well-known algorithms, as disclosed above.

It is notable that within the bandpass of interest q-sequence Q-magnitudes are not uniform. This is in distinct contrast to MLS and Legendre sequences used for recovering oto-acoustic emissions and evoked-responses, in which the sequences used have uniform Q-magnitudes throughout the entire frequency spectrum. This difference may be used to identify pseudo-periodic q-sequences.

When a q-sequence has been selected, it is used to obtain $\tilde{v}(t)$. $\tilde{v}(t)$ is then convolved with a "convolution recovery sequence" r(t) to obtain an estimate of the system waveform (Eq. 7).

$$\tilde{b}(t)=\tilde{v}(t)\Theta r(t) \qquad (7)$$

where $\Theta$ is time-domain convolution.

The convolution recovery sequence r(t) for time-domain convolution of $\tilde{v}(t)$ to recover $\tilde{b}(t)$ is the inverse Fourier transform of the reciprocal of $\{Q_d(f)\}$: (Eq. 8).

$$r(t)=IDFT[1/Q_d(f)] \qquad (8)$$

where IDFT is the Inverse Discrete Fourier Transform which, by computing with complex numbers, also incorporates phase. We adopt the convention in which the usual Fourier 1/N factor is included in the IDFT.

Since r(t) is computed from a set $\{Q_d(f)\}$, it will now be described how the Q-magnitudes of this set are determined. There are several factors that affect the choices:

1. Bandpass limits.
2. Other filtering, including but not limited to Wiener filtering.
3. Adjustment for undesirable Q-magnitudes.

$Q_d(f)$ usually equals $Q_c(f)$ in the bandpass because this allows full and accurate recovery of b(t) (Eq. 4 when $Q_d(f)=Q_c(f)$) But outside the bandpass of interest there is no need to have $Q_d(f)$ equal $Q_c(f)$. In fact, if a $|Q_c(f)|$ at a frequency outside the bandpass is substantially less than unity, then including this $Q_c(f)$ in $\{Q_d(f)\}$ will increase the noise at that frequency (Eq. 4). (This increase in noise occurs in those deconvolution methods that utilize a recovery function based completely upon the stimulation-sequence.) It is most practical to set Q-magnitudes of $|Q_d(f)|$ in bandreject frequencies to maximal values. This reduces to negligible values the effects of these frequencies on $\tilde{b}(t)$ after the convolution of $\tilde{v}(t)$ with r(t). To prevent Gibbs-phenomenon "ringing", the Q-magnitudes in the bandedge frequencies should be progressively increased when moving from the bandpass to the bandreject frequencies. Other digital filtering techniques known to those in the art can be incorporated at this stage in the computation, or in other stages.

One filtering method uses decimation in frequency This is a technique familiar to those skilled in digital filter art, and is particularly applicable if a high A-D rate has been utilized in data collection. By choice of decimation, frequencies with poor Q-magnitudes can be removed from the calculations. The effects on recoverable waveshape of use of decimation need to be carefully evaluated.

If desired, $\{Q_d(f)\}$ can be modified to compensate or adjust for undesirable magnitudes in $\{|Q_c(f)|\}$ in the bandpass, which might otherwise amplify noise relative to other frequencies. Such adjustments can include setting the $|Q_d(f)|$ at a specific frequency to unity, or to a value similar to those of nearby frequencies, or to a maximum. Another possible adjustment is to remove $Q_d(f)$ at some frequencies, and to substitute other $Q_d(f)$ at a nearby frequency that is not an integer multiple of the primary frequency determined by the duration of SL, i.e., at a fractional frequency. This adjustment can be guided by evaluation of the magnitude of $|Q_c(f)|$ at the alternative frequency When such a fractional frequency is used, the phase is also utilized, since the adjusted frequencies are computed from q(t) using complex numbers. It should be noted that any adjustment of the magnitude of a given $|Q_d(f)|$ so as to differ from the magnitude of the $|Q_c(f)|$ at that same frequency will cause inaccuracies in the recovered waveform. Similarly, adjustments to the frequencies in the set $\{Q_d(f)\}$ will also cause inaccuracies in the recovered waveform. Thus, any adjustments must be tested carefully for their effects and should be used sparingly.

There may be occasions when a user must of necessity use a stimulation-sequence that is not a q-sequence as defined in this invention because one or more of the Q-magnitudes in the bandpass are greater than 0.01 and less than 0.5. Such a stimulation-sequence is referred to as a "quasi-q-sequence". It is a teaching and an aspect of the invention that a quasi-q-sequence can be used by adjustment of the $|Q_d(f)|$ at the frequencies where the Q-magnitude is less than 0.5, in the bandpass of interest, as described in the preceding paragraphs.

Once a set $\{Q_d(f)\}$ is chosen, it is used to compute r(t), as given in Eq. 8. Then that r(t) is used in Eq. 7 to deconvolve $\tilde{v}(t)$, yielding $\tilde{b}(t)$, the estimate of b(t). $\tilde{b}(t)$ may not equal b(t) for a number of reasons:

1. Residual noise.
2. $\{|Q_d(f)|\} \neq \{|Q_c(f)|\}$ in the bandpass of interest due to adjustments.
3. Use of fractional frequencies.
4. Filtering of frequencies that are in b(t).
5. Windowing of time-domain functions.

In any of the frequency-domain calculations related to time-domain sequences or data, windowing functions may need to be applied, at some sacrifice in accuracy, as is well known in the art. Hanning and Hamming windowing methods are disclosed in Press et al., *Numerical Recipes in C, The Art of Scientific Computing*, 2nd Ed., (1992) Cambridge Univ Press, at pp. 553–558.

In any case where the SNR is initially low, averaging may be used to improve signal detection. Such averaging can occur from cyclic repetition of q(t) (100% duty cycle), with cyclic accumulation of the sum of repeated $\tilde{v}(t)$, normalized by the number of cycles. In this case $\tilde{v}(t)$ will be a circular vector. When calculating r(t) from the frequency-domain in Eq. 8, r(t) will also be circular. No windowing will be needed.

Another mode of averaging that can be used is a variation on the method of Thornton, et al., (U.S. Pat. No. 5,734,827).

Before describing alternatives and variants of QSD, steps in the use of QSD for detecting individual transient responses from a superposed signal with q-sequences will be summarized:

1. Select user constraints on variables that will affect the choice of q-sequence, including an SI-ratio less than unity and greater than zero, and Q-magnitudes in the bandpass greater than 0.5.
2. Create q(t) by selection process utilizing user constraints.
3. Select the members of the set $\{Q_d(f)\}$ with regard to filtering and adjustments, and then use the set to generate r(t).
4. Deliver stimuli to the system under test at the timings of q(t), with 100% duty cycle if averaging.
5. Collect response data, averaging if necessary.
6. Deconvolve $\tilde{v}(t)$ by convolving $\tilde{v}(t)$ with r(t), thus calculating the estimate $\tilde{b}(t)$.

It will be apparent to those skilled in the art that there are many elements of the above method that are different for different systems. For example, the criteria for q-sequences are likely to be different for different systems, and may well be different even for the same system under different conditions, e.g., different noise. Also, the choices of filtering, and the length of runs during averaging will differ by system, and by user's goals. Hence a series of steps are taught, which, when followed, can lead to an accurate estimation of the system waveform, while leaving to the user the selection of criteria relevant to the specific system under test and to the user's goals.

The following description exemplifies the application of the steps listed above. Assume that the user of the invention, hereafter just called "user", is familiar with a system to be tested, and that the user knows the system-response waveform that occurs when stimuli are applied with a repetition-rate that does not overlap the waveforms. The user also knows the bandpass of that waveform. The user wishes to know if there is any change in the system-response waveform when the repetition-rate is high enough to superpose the waveform. The user, with this goal in mind, chooses a mean repetition-rate for testing that will superpose the waveform. The user, having prior experience with the system can estimate the noise likely to be encountered in the system, and based upon that experience chooses the length of the stimulation-sequence. This choice determines the run length and the number of stimuli in the stimulation-sequence. The user also decides that the Q-magnitudes in the bandpass of interest must be at least unity, and, in this example, decides to test with a small SI-ratio, say 0.1. The user then starts a simulated annealing program found in a standard reference book, and on commonly-available computer-program math libraries. The user inputs to the program various parameters, including those above, as well as those specific to simulated annealing, such as the rate of "cooling". Running the program, the user finds that the simulated annealing program cannot find a stimulation-sequence that meets the parameters chosen. This is likely if a very small jitter is selected along with a short stimulation-sequence and a wide bandpass. The user then alters the parameters, for example increasing the SI-ratio to 0.3, and increasing the length of the stimulation-sequence. Running the program with the new parameters yields a stimulation-sequence that does meet the user's constraints. This stimulation-sequence will be used in the testing.

Before testing, the user studies the Q-magnitudes of the selected stimulation-sequence, and realizes that changes in the waveform due to the higher stimulation rate may add some additional low frequencies to the waveform. The user decides to broaden the bandpass slightly to include a lower frequency. But at that frequency the Q-magnitude is 0.9. The user decides to adjust the Q-magnitude of that frequency to be unity, even though it will distort the signal slightly The user chooses to do this rather than start the selection search again. The user also progressively increases the Q-magnitudes in the bandedge regions, and sets the Q-magnitudes in the bandreject regions to the maximum of the computer's floating point numbers. This effectively adds filtering to the QSD recovery sequence. This set of Q-magnitudes, based upon $|Q_c(f)|$, but adjusted as described, is now the set $\{|Q_d(f)|\}$. Using standard frequency-domain to time-domain programs, the user converts this set to the recovery sequence r(t).

The stimuli are then delivered to the system using the stimulation-sequence, and the response data are acquired so that $\tilde{v}(t)$ has been collected. After alignment, the data is then unoverlapped by convolution of $\tilde{v}(t)$ with r(t). The resulting waveform $\tilde{b}(t)$ is observed by the user, both before and after some additional filtering. (This ends the descriptive example of the use of QSD.)

QSD can be accomplished by a variety of computational methods. By way of example, four different methods are listed:

Time-Domain Methods:
1. QSD by time-domain convolution of $\tilde{v}(t)$ with r(t) (the method described above). r(t) is called the convolution recovery sequence.

Frequency-Domain Method.
2. QSD by transformation of v tilde (t) to the frequency-domain to form V tilde (f), then dividing by $Q_d$ (f), followed by inverse Fourier transformation back to the time-domain. This is the frequency-domain equivalent to time-domain method #1, above. In his use, $Q_d$ (f) is the deconvolution set of Fourier coefficients.

The data output of QSD by any method may be further filtered, in which case the bandpass of the final waveform is the "bandpass of interest", as that term is defined in the present invention. The QSD method can be combined with other signal processing techniques known in the art. If the data is processed during data-acquisition, then it is possible to apply some "stopping rule" to determine the number of sweeps averaged (for example, Elberling, C. & Don, M., *Scand Audiol* 13:187–197, 1984). It also might be desirable to reject some data-points, groups of data-points, or sweeps, due to noise. The QSD method can also be used in conjunction with methods that average with weighting algorithms based upon noise estimates (for example, Gerull, G., Graffunder, A., and Wernicke, M., *Scand Audiol* 25:30–27, 1996), or by application of Wiener filtering (Press et al., *Numerical Recipes in C, The Art of Scientific Computing*, 2nd Ed., (1992) Cambridge Univ Press, Cambridge, at Chap. 13.3). It might also be desirable during the deconvolution to minimize the calculation only to the length needed to recover the response $\tilde{b}(t)$. For these uses, the following formulations can be used.

First, describing averaging of v(t) from sweeps:

$$\overline{v}(t) = \frac{1}{NS(t)} \sum_{i=1}^{NS(t)} [w_i(t) \cdot \tilde{v}_i(t)], \quad t = 0, \ldots, SL-1 \quad (9)$$

where:

$\overline{v}(t)$ = the mean $\tilde{v}(t)$ from averaged sweeps
NS(t) = the number of sweeps contributing to the average at a given time $w_i(t)$=weighting function for the i-th sweep
$\tilde{v}_i(t)$=the v(t) of the i-th sweep
SL=length of stimulation-sequence in number of time-points Second, describing deconvolution of the average by convolution with a recovery sequence (Eq. 10):

$$\tilde{b}(t) = \sum_{\tau=0}^{SL-1} [\bar{v}(\tau) \cdot r(t-\tau)], \quad t = 0, \ldots, DL-1 \quad (10)$$

where:

$\tau$=a time-index for time-domain convolution
DL=length of data deconvolved in number of time-points QSD methods can also be utilized when the recovery of $\tilde{b}(t)$ is computed so that first the deconvolution is calculated, followed by the averaging (as has been described for MLS by Thornton, et al., U.S. Pat. No. 5,734,827). In this ordering of the computational parts, it is possible to reject values of the recovered waveform, as it is accumulated in a "recovery buffer". This also permits immediate calculation of each data point in $\tilde{v}_i(t)$, for example in one embodiment, in a DSP (Digital Signal-Processing) chip. Dropping of data points and the addition of weighting functions could also be incorporated. The formulation of QSD for such use is (Eq. 11):

$$\tilde{b}(\tau) = \frac{1}{NS(\tau)} \sum_{i=1}^{NS(\tau)} \left[ w_i(\tau) \cdot \left[ \sum_{t=0}^{SL-1} v_i(t) \cdot r(\tau-t) \right] \right], \quad (11)$$

$\tau=0, \ldots, DL-1$ where the fully reconstructed waveform $\tilde{b}(\tau)$ ($\tau=0, \ldots, DL-1$) is identical to the deconvolved waveform $\tilde{b}(t)$ ($t=0, \ldots, DL-1$).

Another useful procedure that is applicable to QSD is the method of using two stimulations simultaneously by stimulating at two different repetition-rates (Marsh, R., *Ear and Hearing*, 14:169–174,1993). As applied to QSD, there would be two stimulation-sequences of different lengths. Using QSD, it would be feasible to stimulate with two different stimuli, each stimulus being timed by its own stimulation-sequence. A judicious choice of lengths keeps the two sequences from being a multiple of the other, so as to prevent harmonic beating. The system output is separately deconvolved twice, with a separate recovery-sequence for each of the two stimulation-sequences. A variant of this procedure consists of having one stimulus at a uniform repetition-rate, while the other stimulus is timed by a q-sequence. In this variant the uniform-rate response is recovered by averaging of the system output, while the response to the q-sequence stimuli is recovered by deconvolving the system output.

The estimated system-response waveform produced by the invention may not be the ultimate goal of the user. In such a case there may be additional processing of the information in the QSD waveform, so that the final output may not be a waveform. For this reason, display means 50 in FIG. 1 is shown for didactic purposes, but does not represent a required component of QSD. Also, if the final output only utilizes a portion of the bandpass of interest, then the frequencies so utilized can become the "bandpass of interest" within the meaning of this invention.

When computing numerically-intensive processes, it is useful to describe groups of numbers as being contained in "buffers". Such buffers can be physically-distinct elements on a computer board, or elements in a chip, or locations on a magnetic storage medium. Such buffers can also be portions of a digitized memory that are dynamically allocated to store the numbers during the computation. Finally, a "buffer" can be a symbolic representation of a storage method, irrespective of the physical embodiment. All of these alternative buffer methods are applicable to this invention.

EXAMPLE ONE

Methods, Q-Sequence Selection:

Based upon prior user experience with the system being tested in this example, the following parameters for the q-sequence were established:

1. A-D rate=48 kHz (because A-D/D-A equipment used was designed for music audio equipment compatible with CD specifications).
2. Sequence length=504 ms.
3. Stimulus repetition-rate=41.66 stimuli per sec.
4. Maximum jitter±+12% of mean (this equals an SI-ratio of 0.27)
5. Waveform bandpass=30–150 Hz
6. Search cost function=Q-magnitudes in bandpass>2.2

Using a 50 MHz computer running the Linux operating system, the selection process using simulated annealing took several hours. The sequence selected met all the criteria, having Q-magnitudes in bandpass >2.2. The sequence was used in obtaining the recordings.

Methods, Other:

Normal-hearing adult subjects sat in a comfortable chair with a head rest, and watched video tapes of silent movies. Recordings were made in an electrically-shielded, sound-attenuating chamber. Potentials were recorded between vertex and mastoid electrodes. All recordings are plotted with vertex-positive up. The binaural stimuli from a wall-mounted loudspeaker in front of the subject were tone-pips 8 ms long, with a center frequency of 2 kHz, at an intensity less than 60 dB SL, presented at a mean repetition-rate of 41.66 Hz. The preamplifier bandpass filter settings were 0.3 to 500 Hz. The A-D conversion rate was 48 kHz per channel. The evoked responses were averaged over an interval of 500 ms. 1500 sweeps were averaged. The circular average was bandpass filtered at 30–150 Hz during deconvolution.

Figure 2:
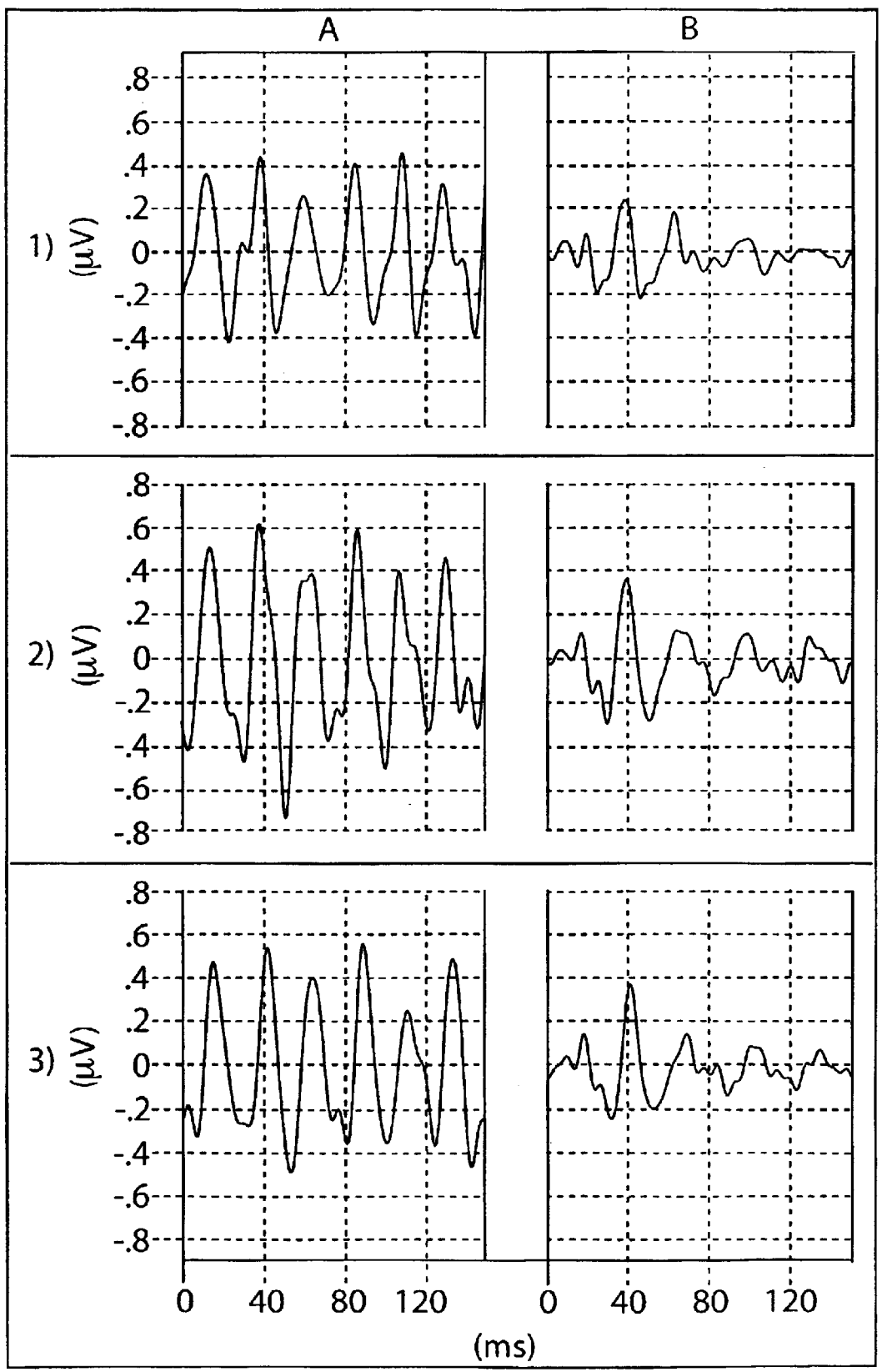
FIG. 2, column A shows recordings of brain waves using the invention, the waves being superposed responses.

Results:

Data taken from three subjects are shown in FIG. 2. The numbers to left of column A are the numbers that identify the three subjects. The abscissa is time in milliseconds, the ordinate is voltage magnitude, referred to the electrodes. Although the sweep length was 500 ms, only the first 150 ms are shown.

Averaged convolved (superposed) responses are shown in column A of FIG. 2. These waveforms are referred to in the literature as "the 40-Hz response". These waveforms, in the description above of the current invention, are averaged $\tilde{v}(t)$.

When these averages were deconvolved to provide an estimate of the system-response waveform $\tilde{b}(t)$, the response to each stimulus in the stimulus-sequence was revealed, as shown in column B of FIG. 2. Although the deconvolution computation was carried out to 500 ms, only the first 150 ms are shown. Note that the responses in column B of FIG. 2 have a peak at about 40 ms. In contrast, the stimuli were delivered with a stimulation-sequence timing SI of 24±2.9 ms. Clearly, the responses are longer than any SI. Waveforms having this characteristic have been observed in more than 50 subjects, using the methods and apparatuses of the invention.

TABLE

This Table contains acronyms and the terms used in Eqs. 1–5, 7, 8. Terms in the other equations are defined in the vicinity of the equation. This table also includes some of the terms that are specifically defined for use in the invention. If any of the time-indexed functions below are transformed to the frequency-domain, then they are capitalized and indexed by frequency.

·=multiplication symbol alignment signal=a signal used to align, with respect to timing or phase, two recordings or a recording and a template.

A-D=Analog-to-Digital bandpass of interest=those frequencies necessary to display or use the estimated system-response waveform or a further filtering of that waveform, or those frequencies needed for a user's final output, or those frequencies that are needed for providing information for a user's goal.

b(t)=the response, as recorded on a given data-recording channel, to an individual stimulus in the sequence.

$\hat{b}(t)$=the estimate of b(t) from deconvolution of $\tilde{v}(t)$.

©=special-case time-domain convolution, where convolution includes use of q(t).

D-A=Digital-to-Analog definitive time pattern=a pattern that conforms to a rule set containing both time-domain and frequency-domain rules.

duty cycle=the percentage time that a given device is "on".

Fourier coefficient vector magnitude=the vector sum of the real and imaginary Fourier components at a specified frequency in a Q-magnitude calculation (Eq. 6).

IDFT=the Inverse Discrete Fourier Transform.

MLS=Maximum-Length Sequence n(t)=additive, nonconvolved noise, not synchronized with the stimuli. (Instrumental noise, and noise from external sources are included in this term.)

Pseudo-periodic sequence=a sequence of stimuli in which the SIs are not uniform, and where the SI-ratio is between 0 and 1.

Q(f)=the real and imaginary Fourier coefficients at frequency f.

|Q(f)|=the magnitude of the Fourier coefficient vector at frequency f.

{Q(f)}=the set of all Q(f) at all frequencies, or a subset of same.

{|Q(f)|}=the set of all |Q(f)| at all frequencies, or a subset of same.

$Q_c(f)$=the real and imaginary Fourier coefficients from special-case convolution at frequency f, as determined by q(t).

$|Q_c(f)|$=the |Q(f)| during special-case convolution at frequency f, as determined by q(t).

$Q_d(f)$=the real and imaginary Fourier coefficients used during deconvolution, at frequency f as determined by the user.

$|Q_d(f)|$=the |Q(f)| used during deconvolution, at frequency f, as determined by the user.

Q-magnitude=the magnitude of the vector of the Fourier coefficient, |Q(f)| (given in Eq. 6). Q-magnitudes can have values between zero and a number equal to the number of stimuli in the stimulation-sequence for which the Q-magnitudes are being computed.

q-sequence=a sequence of 1's and zero's in which the 1's indicate timing for stimuli. A q-sequence is pseudo-periodic, has a definitive time pattern, and conforms to a rule set with both time-domain and frequency-domain constraints. A q-sequence has an SI-ratio less than unity and greater than zero. The frequency-domain constraints include Q-magnitudes in the bandpass of interest of 0.5 or greater.

QSD=q-sequence deconvolution, where the letters in the acronym are capitalized because they are a title in an acronym.

q(t)=stimulus sequence timing. (This consists of 1's and 0's in a discrete-time pattern, and precisely describes the timing-pattern of the stimuli.)

quasi-q-sequence=a sequence of 1's and zero's in which the 1's indicate timing for stimuli. A quasi-q-sequence is pseudo-periodic, has a definitive time pattern, and conforms to a rule set with both time-domain and frequency-domain constraints. A quasi-q-sequence has an SI-ratio less than unity and greater than zero. The frequency-domain constraints include Q-magnitudes in the bandpass of interest of greater than 0.01 and less than 0.5.

r(t)=the recovery function for time-domain convolution.

SI=Stimulus Interval start-to-start. The term "stimulus interval" means the same as SI and is used interchangeably with SI.

SI-ratio=$(SI_{max}-SI_{min})/(SI_{min})$

SL=Sequence Length (Also means "Sensation Level" in dBSL)

superposed=having been obtained by superposition.

superposition=the process by which a discrete-time waveform is the algebraic summation at each time-point of two or more time-aligned waveforms, or the same waveform with one or more time-shifts, or two or more time-shifted waveforms.

synchronization signal=a signal used to synchronize two cyclic processes so that they operate at the same frequency.

system=any physical or biological entity that provides a response due to stimulation.

Θ=time-domain convolution v(t)=the superposed waveforms of b(t), when b(t) is special-case convolved [©] with q(t).

$\tilde{v}(t)$=v(t) with added noise (n(t)).

CHANGES AND MODIFICATIONS

Without departing from the spirit and scope of this invention, one of ordinary skill can make various changes and modifications to the invention to adapt it to various usages and conditions. As such, these changes and modifications are properly, equitably and intended to be, within the full range of equivalence of the following claims.

What is claimed is:

1. An apparatus for creating a recording of a system output composed of superposed waveforms, said system output arising from a tested system, said system tested with stimuli, said system output having an associated estimated system-response waveform, said estimated system-response waveform having frequencies of interest within a bandpass of interest, said apparatus comprising: (a) At least one stimulus-generating means that stimulates said tested system, said stimulus-generating means generating at least one sequence of stimuli with a timing pattern, said timing pattern being that of a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass of interest is 0.5 or greater, (b) At least one data-acquisition means including a recording means, said recording means recording at least one of the following: (1) only said system output to form a system-output-only recording, (2) both the system output from said tested system and an alignment signal to form both a system output recording and an alignment signal recording, said alignment signal being correlated with said timing pattern.

2. The apparatus of claim 1, further comprising at least one additional component, wherein said component is selected from the group consisting of: synchronizing means, averaging means, filtering means, amplifying means, data-rejection means, data-acquisition stopping means, simultaneous multiple q-sequence data-acquisition means, simultaneous multiple q-sequence data-acquisition including at least one uniform stimulation-sequence means, Q-magnitude adjustment means, deconvolution set magnitude adjustment means, deconvolution set frequency adjustment means, data-analysis means, computational means, intermediate-data computational means, intermediate-data analysis means, display means, and outputting means.

3. An apparatus for calculating an estimated system-response waveform from a system output composed of superposed waveforms, said system output arising from a tested system, said system tested with stimuli, said system output having an associated estimated system-response waveform, said estimated system-response waveform having frequencies of interest within a bandpass of interest, said stimuli having been generated by a stimulus-generating means, said stimulus-generating means generating at least one stimulation-sequence having a timing pattern, said timing pattern being a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, wherein the vector magnitude of each said Fourier coefficient of said q-sequence within aid bandpass of interest is 0.5 or greater, said system output having been recorded by recording means, said recording means recording at least one of the following: (1) only said system output to form a system-output-only recording, (2) both the system output from said tested system and an alignment signal to form both a system output recording and an alignment signal recording, said alignment signal being correlated with said timing pattern, wherein at least one of the following has been transmitted: (1) said system-output-only recording, (2) both said system output recording and alignment signal recording, said apparatus comprising: (a) inputting means, said inputting means receiving said system output recording and said alignment signal recording; (b) data-analysis means that calculates said estimated system-response waveform by deconvolution means, said deconvolution means operating on at least one of the following: (1) said system-output-only recording, (2) both said system output recording and said alignment signal recording.

4. The apparatus of claim 3, further comprising at least one additional component, wherein said component is selected from the group consisting of: averaging means, filtering means, amplifying means, noise-estimation means, data-rejection means, sweep-rejection means, simultaneous multiple stimulation-sequence data-analysis means, simultaneous multiple stimulation-sequence data-analysis including at least one uniform stimulation-sequence means, decimation by frequency means, decimation by time means, Q-magnitude adjustment means, deconvolution set magnitude adjustment means, deconvolution set frequency adjustment means, computational means, intermediate-data computational means, intermediate-data analysis means, waveform-analysis means for analyzing said estimated system-response waveform, display means, outputting means.

5. An apparatus for calculating an estimate of a system-response waveform from a system output composed of superposed waveforms, said system output arising from a tested system, said system tested with stimuli, said system output having an associated estimated system-response waveform, said estimated system-response waveform having frequencies of interest within a bandpass of interest, said apparatus comprising: (a) At least one stimulus-generating means that stimulates said tested system, said stimulus-generating means utilizing at least one timing pattern, said timing pattern being a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass of interest is 0.5 or greater, (b) data-acquisition means that includes a recording means, said recording means recording at least one of the following: (1) only said system output to form a system-output-only recording, (2) both the system output from said tested system and an alignment signal to form both a system output recording and an alignment signal recording, said alignment signal being correlated with said timing pattern, (c) data-analysis means that calculates said estimated system-response waveform by deconvolution means, said deconvolution means operating on at least one of the following: (1) said system-output-only recording, (2) both said system output recording and said alignment signal recording.

6. The apparatus of claim 5, further comprising at least one additional component, wherein said component is selected from the group consisting of: averaging means, filtering means, amplifying means, noise-estimation means, data-rejection means, sweep-rejection means, simultaneous multiple stimulation-sequence data-analysis means, simultaneous multiple stimulation-sequence data-analysis including at least one uniform stimulation-sequence means, decimation by frequency means, decimation by time means, Q-magnitude adjustment means, deconvolution set magnitude adjustment means, deconvolution set frequency adjustment means, computational means, intermediate-data computational means, intermediate-data analysis means, waveform-analysis means for analyzing said estimated system-response waveform, display means, outputting means.

7. An apparatus as in any of claims 3 and 5, wherein said data-analysis means further comprises at least one deconvolution mean selected from the group consisting of: time-domain convolution of the system output by a convolution recovery sequence; time-domain cross-correlation of the system output by cross-correlation recovery-sequence; division in the frequency-domain of the system output by a deconvolution set of Fourier coefficients; multiplication of said system output by an inversion of a circulant matrix derived from a convolution recovery sequence; filtering in the time-domain; filtering in the frequency-domain; deconvolution of single sweeps; deconvolution of combinations of one or more single sweeps; deconvolution of subaverages.

8. An apparatus for calculating an estimate of a system-response waveform from a system output composed of sequential data-samples, said sequential data-samples being comprised of superposed waveforms, said system output arising from a tested system, said system tested with stimuli, said system output having an associated estimated system-response waveform, said estimated system-response waveform having a length, said estimated system-response waveform having frequencies of interest within a band pass of interest, said apparatus comprising: (a) At least one stimulus-generating means that stimulates said tested system, said stimulus-generating means utilizing at least one timing pattern, said timing pattern being a q-sequence, said q-sequence having a length, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass of interest is 0.5 or greater, (b) data-acquisition means that includes a recording means, said recording means recording at least one of the following: (1) only said system output to form a system-output-only recording, (2) both the system output from said tested system and an alignment signal to form both a system output recording and an alignment signal recording, said alignment signal being correlated with said timing pattern, (c) data-analysis means that calculates said estimated system-response waveform by deconvolution means, said deconvolution means operating on at least one of the following (1) said system-output-only recording (2) both said system output recording and said alignment signal recording from (b), said data-analysis means further comprising: (1) a data-sample buffer having a length of at least one said data-sample, (2) a recovery-sequence buffer, said recovery-sequence buffer having a length equal to the said length of the said q-sequence, said recovery-sequence buffer having contents, said contents being the numerical values of said recovery-sequence, (3) a reconstruction buffer, said reconstruction buffer having a length at least as great as said length of said estimated system-response waveform, (4) a deconvolving means that deconvolves each data-sample with said contents of said recovery-sequence buffer to create a deconvolution, (5) a summing means that sums said deconvolutions in said reconstruction buffer.

9. An apparatus of any of claims 1, 3, 5, and 8, further comprising intermediate-data computational means, wherein said system output is composed of sequential sweeps, said sequential sweeps being composed of sequential data-samples corresponding to a single cycle of said q-sequence, said intermediate-data computational means comprising: (a) at least one deconvolution-storage buffer and at least one reconstruction buffer, each said buffer having a length, said deconvolution-storage buffer having a length equal to said length of said reconstruction buffer, said deconvolution-storage buffer having places corresponding to places in said reconstruction buffer, (b) deconvolution means further comprising at least one of the following: (1) single sequential sweep deconvolution means that deconvolves each said sequential sweep and sums said deconvolutions in said deconvolution-storage buffer for at least one sweep, forming an intermediate deconvolution waveform, (2) summing means that sums two or more said sequential sweeps in a summing buffer and then deconvolves the contents of said summing buffer, forming an intermediate deconvolution waveform.

10. An apparatus of claim 9, wherein said intermediate computational means further comprises at least one intermediate-data analysis means selected from the group consisting of: (a) data-rejection means and signal-summation means, said data-rejection means analyzing said intermediate deconvolution waveform, comparing said analysis with a predetermined limit to create a sweep-rejection value, said signal-summation means multiplying said places of said deconvolution-storage buffer by said sweep-rejection value, then summing the product into said corresponding place in said reconstruction buffer, and then clearing the said deconvolution-storage buffer. (b) stopping means, wherein said stopping means operates by forming a noise estimate, said noise estimate being based upon cyclic analysis of said intermediate deconvolution waveform, wherein said stopping means further operates by forming a signal estimate, said signal estimate being based upon cyclic analysis of said reconstruction buffer, wherein said stopping means compares said noise estimate and said signal estimate to predetermined limits, said stopping means stopping said data-acquisition if at least one predetermined limit is reached. (c) data-weighting means, wherein said intermediate-data waveform is composed of data-samples, said data-weighting means applying a weighting function to at least one data-sample, said weighting function based upon predetermined features of said intermediate-data waveform, said predetermined features being detected during cyclic data-analysis of intermediate-data waveforms by said data-weighting means.

11. An apparatus as in any of claims 1, 3, 5, and 8, wherein q-sequence generating means produces first q-sequence and second q-sequence, wherein said first q-sequence has a length not equal to the length of said second q-sequence, wherein stimulus-generating means consists of first stimulus-generating means and second stimulus-generating means, wherein said first stimulus-generating means utilizes said first q-sequence for stimulus timing, and wherein said second stimulus-generating means utilizes said second q-sequence for stimulus timing, said first stimulus-generating means and said second stimulus-generating means operating simultaneously with said data-acquisition means, wherein said tested system generates first estimated system-response waveform from stimuli from first stimulus-generating means and second estimated system-response waveform from stimuli from second stimulus-generating means, and wherein said data-analysis means deconvolves said first estimated system-response waveform from said system output by means of first q-sequence and deconvolves said second estimated system-response waveform from said system output by means of second q-sequence.

12. An apparatus as in any of claims 1, 3, 5, and 8, further comprising uniform-sequence generating means, wherein q-sequence generating means produces at least one q-sequence, and wherein uniform-sequence generating means produces at least one uniform sequence, wherein said q-sequence has a length not equal to the length of said uniform sequence, wherein stimulus-generating means is comprised of first stimulus-generating means and second stimulus-generating means, wherein said first stimulus-generating means utilizes said q-sequence for timing of stimuli from first stimulus-generating means, and wherein said second stimulus-generating means utilizes said uniform sequence for timing of stimuli from second stimulus-generating means, said first stimulus-generating means and said second stimulus-generating means operating simultaneously with said data-acquisition means, wherein said tested system generates first estimated system-response waveform from stimuli from first stimulus-generating means and second estimated system-response waveform from stimuli from second stimulus-generating means, and wherein said data-analysis means comprises a first data-analysis means and second data-analysis means, wherein said first data-analysis means deconvolves said first estimated system-response waveform from said system output by means of q-sequence, and wherein said second data-analysis means averages said second estimated system-response waveform from said system output by means of said uniform sequence.

13. An apparatus for calculating an estimate of a system-response waveform from a system output composed of superposed waveforms, said system output arising from a tested system, said system tested with stimuli, said system output having an associated estimated system-response waveform, said estimated system-response waveform having frequencies of interest within a bandpass of interest, said apparatus comprising: (a) stimulus-generating means that stimulates said tested system, said stimulus-generating means utilizing at least one timing pattern, said timing pattern being a quasi q-sequence, wherein said quasi-q-sequence is a pseudo-periodic sequence having a definitive time pattern, wherein said quasi-q-sequence has associated frequencies, said frequencies each having an associated Fourier coefficient vector magnitude, said coefficient vector magnitude ranging between zero and the number of stimuli in said quasi-q-sequence, wherein the vector magnitude of each said Fourier coefficient of said quasi-q-sequence within said bandpass of interest is less than 0.5 and greater than 0.01, (b) data-acquisition means that includes a recording means, said recording means recording at least one of the following: (1) only said system output to form a system-output-only recording, (2) both the system output from said tested system and an alignment signal to form both a system output recording and an alignment signal recording, said alignment signal being correlated with said timing pattern, (c) data-analysis means that calculates said estimate of system-response waveform by a deconvolution means, said deconvolution means operating on at least one of the following: (1) said system-output-only recording, (2) both said system output recording and said alignment signal recording from (b), said deconvolution means utilizing deconvolution Fourier vector coefficients, at least one of said deconvolution Fourier vector coefficients in the bandpass of interest being adjusted, wherein said adjusted deconvolution Fourier vector coefficient has a magnitude not equal to the magnitude of the Fourier vector coefficient at the same frequency calculated from said quasi-q-sequence in (a).

14. A method for estimating a system-response waveform from a system output composed of superposed waveforms, said system output arising from a tested system, said system tested with stimuli, said system output having an associated estimated system-response waveform, said estimated system-response waveform having frequencies of interest within a bandpass of interest, said method comprising: (a) stimulating said tested system with a sequence of stimuli utilizing at least one timing pattern, said timing pattern being a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass is 0.5 or greater, (b) recording at least one of the following: (1) only said system output forming a system-output-only recording, (2) both the system output from said tested system and an alignment signal to form both a system output recording and an alignment signal recording, said alignment signal being correlated with said q-sequence.

15. A method for estimating a system-response waveform from a system output composed of superposed waveforms, said system output arising from a tested system, said system tested with stimuli, said system output having an associated estimated system-response waveform, said estimated system-response waveform having frequencies of interest within a bandpass of interest, stimulating said tested system with a sequence of stimuli utilizing at least one timing pattern, said timing pattern being a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass is 0.5 or greater, recording at least one of the following: (1) only said system output forming a system-output-only recording, (2) both the system output from said tested system and an alignment signal to form both a system output recording and an alignment signal recording, said alignment signal correlated with said q-sequence, and transmitting at least one of the following: (1) only said system-output-only recording, (2) both said system output recording and said alignment signal recording, said method comprising: (a) inputting at least one of the following: (1) only said system-output-only recording, (2) both said system output recording and said alignment signal recording, (b) estimating said system-response waveform by deconvolution operating on at least one of the following: (1) said system-output-only recording, (2) both said system output recording and said alignment signal recording.

16. A method for estimating a system-response waveform from a system output composed of superposed waveforms, said system output arising from a tested system, said system tested with stimuli, said system output having an associated estimated system-response waveform, said estimated system-response waveform having frequencies of interest within a bandpass of interest, said method comprising: (a) stimulating said tested system with a sequence of stimuli utilizing at least one timing pattern, said timing pattern being a q-sequence, wherein said q-sequence is a pseudo-periodic sequence having a definitive time pattern, wherein said q-sequence has a maximum stimulus-interval ratio less than unity and greater than zero, wherein said q-sequence has associated frequencies, said frequencies each having an associated Fourier coefficient vector magnitude, said coefficient vector magnitude ranging between zero and the number of stimuli in said q-sequence, and further wherein the vector magnitude of each said Fourier coefficient of said q-sequence within said bandpass is 0.5 or greater, (b) recording at least one of the following: (1) only said system output forming a system-output-only recording, (2) both said system output from said tested system and said alignment signal to form both a system output recording and an alignment signal recording, said alignment signal being correlated with said q-sequence, (c) estimating said system-response waveform by deconvolution operating on at least one of the following: (1) said system-output-only recording, (2) both said system output recording and said alignment signal recording.

17. A method of any of claims 15 and 16 wherein estimating system-response waveform by deconvolving further comprises at least one deconvolution method selected from the group consisting of: time-domain convolution of the system output by a convolution recovery sequence; time-domain cross-correlation of the system output by a cross-correlation recovery-sequence; division in the frequency-domain of the system output by a deconvolution set of Fourier coefficients; multiplication of said system output by an inversion of a circulant matrix derived from a convolution recovery sequence; filtering in the time-domain; filtering in the frequency-domain; deconvolution of single sweeps; deconvolution of combinations of one or more single sweeps; deconvolution of subaverages.

18. A method of any of claims 14, 15, and 16, wherein the method further comprises at least one additional method, wherein said additional method is selected from the group consisting of: averaging method, filtering method, amplifying method, noise-estimation method, data-rejection method, sweep-rejection method, simultaneous multiple stimulation-sequence data-analysis method, simultaneous multiple stimulation-sequence data-analysis including at least one uniform stimulation-sequence method, decimation by frequency method, decimation by time method, Q-magnitude adjustment method, deconvolution-set magnitude-adjustment method, deconvolution-set frequency-adjustment method, computational method, intermediate-data computational method, intermediate-data analysis method, waveform-analysis method for analyzing said estimated system-response waveform, display method, outputing method.

19. A method of any of claims 14, 15, and 16, wherein said system output is composed of data-samples, wherein said data-analysis method further comprises at least one calculating method selected from the group consisting of: calculating method that applies a weighting function to at least one data-sample, said weighting function based upon predetermined features of said system output, said features detected during data-analysis by said calculating method; stopping-rule calculating method that calculates a noise estimate, said noise estimate based upon said data-sample , wherein said calculating method compares said noise estimate with a predetermined limit and stops said data-acquisition method when said predetermined limit has been reached.

20. The method of any of claims 14, 15, and 16, wherein the system output is selected from the group consisting of: a signal generated by a nervous system of a living organism; a signal generated by a component of nervous system; a signal generated by a sensory system; a signal generated by a visual system; a signal generated by an auditory system; a signal generated by a somatosensory system; a superposed evoked-response; a superposed auditory evoked-response; a superposed oto-acoustic emission; a superposed auditory brainstem-response; a superpose auditory middle-latency response; a superposed auditory G-wave; a superposed electoretinogram; a superposed visual-evoked response; a superposed somatosensory-evoked response.

21. The method of any of claims 14, 15, and 16, wherein the system output is evaluated in a screening test in which the stimulus repetition-rate of an evoked-response is above stimulus fusion.

22. The method of any of claims 14, 15, and 16, wherein the system output is evaluated in a screening test in which the time from start of a stimulus to the start of the next stimulus has a duration that is longer than the duration of the system-response waveform evoked by each individual stimulus.

23. A digital computer programmed with controlling software, wherein said controlling software comprises the method of any of claims 14, 15, and 16.

* * * * *